United States Patent
Sugihara et al.

(10) Patent No.: US 6,274,806 B1
(45) Date of Patent: Aug. 14, 2001

(54) PLATINUM COMPLEX FOR USE AS SENSITIZER FOR SEMICONDUCTOR ELECTRODE OF SOLAR CELL

(75) Inventors: Hideki Sugihara; Kohjiro Hara; Kazuhiro Sayama; Hironori Arakawa; Ashraful Islam; Lok Pratap Singh, all of Tsukuba (JP)

(73) Assignee: Agency of Industrial Science and Technology (JP)

( * ) Notice: Subject to any disclaimer, the term of this patent is extended or adjusted under 35 U.S.C. 154(b) by 0 days.

(21) Appl. No.: 09/534,963

(22) Filed: Mar. 27, 2000

(30) Foreign Application Priority Data

Mar. 8, 2000 (JP) .................................................. 12-064059

(51) Int. Cl.$^7$ .......................... H01G 9/20; H01M 14/00; H01L 31/04
(52) U.S. Cl. .......................... 136/263; 136/252; 429/111; 429/212; 429/213; 257/40; 257/428; 257/431; 257/439; 556/136; 556/137; 544/225; 546/2; 546/8; 546/10
(58) Field of Search ..................................... 136/263, 252; 429/111, 212, 213; 257/40, 428, 431, 439; 556/136, 137; 544/225; 546/2, 8, 10

(56) References Cited

U.S. PATENT DOCUMENTS

| 5,028,467 | * | 7/1991 | Maruyama et al. | 428/64.9 |
| 5,705,664 | * | 1/1998 | Schulz et al. | 556/113 |
| 5,728,590 | * | 3/1998 | Powell | 436/547 |
| 5,766,952 | * | 6/1998 | Mann et al. | 436/2 |
| 6,043,428 | * | 3/2000 | Han et al. | 136/263 |

FOREIGN PATENT DOCUMENTS

| 258655 | * | 3/1988 | (EP) . |
| 975026 | * | 1/2000 | (EP) . |
| WO 91/16719 | * | 10/1991 | (WO) . |
| WO 94/04497 | * | 3/1994 | (WO) . |
| WO 98/50393 | * | 11/1998 | (WO) . |

OTHER PUBLICATIONS

Zuleta et al., J. Am. Chem. Soc., 111, pp. 8916–8917, Nov. 1989.*
Cummings et al, J. Am. Chem. Soc., 118, pp. 1949–1960, Feb. 1996.*
Islam et al, New J. Chem., 24, pp. 343–345, May 2000.*

* cited by examiner

Primary Examiner—Alan Diamond
(74) Attorney, Agent, or Firm—Lorusso & Loud

(57) ABSTRACT

A platinum complex represented by the formula $PtL^1/L^2$ or $PtLX^1/LX^2$ wherein $L^1$ and L each represent a ligand selected from the group consisting of 2,2'-bipyridine compounds having at least one anionic group and 1,10-phenanthroline compounds having at least one anionic group, $L^2$ represents a dithiolate selected from those represented by the formulas (a) through (d) shown in the specification, and $X^1$ and $X^2$ each represent a thiolate selected from those represented by the following formulas (e) and (f) shown in the specification. A dye-sensitized electrode includes a substrate having an electrically conductive surface, an oxide semiconductor film formed on the conductive surface, and the above platinum complex supported on the film. A solar cell includes the above electrode, a counter electrode, and an electrolyte disposed therebetween.

6 Claims, No Drawings

PLATINUM COMPLEX FOR USE AS SENSITIZER FOR SEMICONDUCTOR ELECTRODE OF SOLAR CELL

BACKGROUND OF THE INVENTION

This invention relates to a platinum complex useful for sensitizing an oxide semiconductor electrode of a solar cell. The present invention is also directed to an electrode using the above platinum complex sensitizer and to a solar cell using such an electrode.

With a view toward improving efficiency in conversion of photoenergy into electric energy, many attempts have been hitherto made to expand sensible region of a semiconductor electrode. One known method is dye sensitization. Known sensitizers which are generally ruthenium complexes, however, are not fully satisfactory from the standpoint of practical use.

SUMMARY OF THE INVENTION

It is an object of the present invention to provide a novel platinum complex useful as a sensitizer for an oxide semiconductor electrode of a solar cell.

Another object of the present invention is to provide a platinum complex sensitizer which can absorb light of a visible region and which has a high efficiency of conversion of photo energy to electric energy.

It is a further object of the present invention to provide a dye-sensitized oxide semiconductor electrode useful for a solar cell.

It is a further object of the present invention to provide a solar cell using the above solar cell.

In accomplishing the foregoing object there is provided in accordance with the present invention a platinum complex represented by the following formula (1):

$$PtL^1L^2 \quad (1)$$

wherein
$L^1$ represents a ligand selected from the group consisting of 2,2'-bipyridine compounds having at least one anionic group and 1,10-phenanthroline compounds having at least one anionic group and
$L^2$ represents a dithiolate selected from the group consisting of those represented by the following formulas (a) through (d):

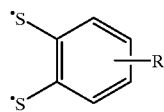

(a)

wherein R represents an alkyl group having 1 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom,

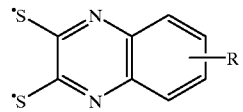

(b)

wherein R represents an alkyl group having 1 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom,

(c)

wherein R and $R^1$ represent, independently from each other, an alkyl group having 1 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom,

(d)

wherein R and $R^1$ represent, independently from each other, an alkyl group having 1 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom.

The present invention also provides a platinum complex represented by the following formula (2):

$$PtLX^1X^2 \quad (2)$$

wherein
L represents a ligand selected from the group consisting of 2,2'-bipyridine compounds having at least one anionic group and 1,10-phenanthroline compounds having at least one anionic group and
$X^1$ and $X^2$ represent, independently from each other, a thiolate selected from the group consisting of those represented by the following formulas (e) and (f):

(e)

wherein R represents an alkyl group having 1 to 6 carbon atoms, an alkenyl group having 2 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom,

(f)

wherein Ar represents a substituted or non-substituted aryl group having 6 to 10 carbon atoms.

The present invention further provides a dye-sensitized electrode comprising a substrate having an electrically conductive surface, an oxide superconductor film formed on said conductive surface, and the above platinum complex supported on said film.

The present invention further provides a solar cell comprising the above electrode, a counter electrode, and an electrolyte disposed therebetween.

Other objects, features and advantages of the present invention will become apparent from the detailed description of the preferred embodiments of the invention to follow.

DETAILED DESCRIPTION OF THE PREFERRED EMBODIMENTS OF THE INVENTION

In the platinum complex of the formula (1), $L^1$ represents a ligand selected from 2,2'-bipyridine compounds having at least one anionic group and 1,10-phenanthroline compounds having at least one anionic group. The anionic group may be, for example, a carboxyl group, a sulfonic acid group or phosphoric acid group. The anionic group may be a free acid group or its neutral salt group neutralized with a salt forming anion such as an alkali metal ion (e.g. Na or K ion) or ammonium ion. The number of the anionic groups contained in the ligand $L^1$ is at least one, preferably at least two. The number of the anionic groups is generally 4 (four) at maximum.

Examples of 2,2'-bipyridine compounds having at least one anionic group may be those represented by the following formula (3):

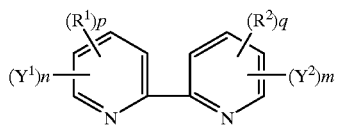

wherein $Y^1$ and $Y^2$ stands, independently from each other, for an anionic group, $R^1$ and $R^2$ stands, independently from each other, for a substituent which may be, for example, an alkyl group having 1 to 4 carbon atoms, a halogen atom such as chlorine, bromine, iodine or fluorine or a halogenated alkyl group having 1 to 4 carbon atoms, m and n are integers of 0 to 4, preferably 1 to 2, and p and q are integers of 0 to 6, preferably 0 to 2. A total of m and n is preferably 1 to 6, more preferably 2.

Illustrative of the bipyridine compounds are 2,2'-bipyridine-4,4'-dicarboxylic acid, 2,2'-bipyridine-4,4'-disulfonic acid, 2,2'-bipyridine-4,4'-diphosphoric acid, 2,2'-bipyridine-5,5'-dimethyl-4,4'-dicarboxylic acid, 2,2'-bipyridine-5,5'-dimethyl-4,4'-disulfonic acid and 2,2'-bipyridine-5,5'-dimethyl-4,4'-diphosphoric acid.

Examples of 1,10-phenanthroline compounds having at least one anionic group may be those represented by the following formula (4):

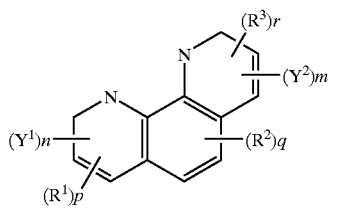

wherein $Y^1$ and $Y^2$ stands, independently from each other, for an anionic group, $R^1$, $R^2$ and $R^3$ stand, independently from each other, for a substituent which may be, for example, an alkyl group having 1 to 4 carbon atoms, a halogen atom such as chlorine, bromine, iodine or fluorine or a halogenated alkyl group having 1 to 4 carbon atoms, m and n are integers of 0 to 4, preferably 1 to 2, and p, q and r are integers of 0 to 6, preferably 0 to 2. A total of m and n is preferably 1 to 4, more preferably 2.

Illustrative of suitable 1,10-phenanthroline compounds are 1,10-phenanthroline-4,7-dicarboxylic acid, 1,10-phenanthroline-4,7-disulfonic acid, 1,10-phenanthroline-4,7-diphosphoric acid, 1,10-phenanthroline-3,8-dimethyl-4,7-dicarboxylic acid, 1,10-phenanthroline-3,8-dimethyl-4,7-disulfonic acid and 1,10-phenanthroline-3,8-dimethyl-4,7-diphosphoric acid.

In the platinum complex of the formula (1), $L^2$ represents a dithiolate selected from those represented by the formulas (a) through (d) above.

In the dithiolates of the formulas (a) through (d), the alkyl group represented by R and $R^1$ has 1 to 6 carbon atoms, preferably 1 to 4 carbon atoms and may be, for example, methyl, ethyl, propyl or butyl.

The alkoxyalkyl group represented by R and $R^1$ has 2 to 12 carbon atoms, preferably 3 to 6 carbon atoms, and is preferably represented by the following formula (5):

$$R^4OR^5— \qquad (5)$$

in which $R^4$ represents an alkyl group having 1 to 6 carbon atoms, preferably 1 to 4 carbon atoms and $R^5$ represents an alkylene group having 1 to 6 carbon atoms, preferably 2 to 4 carbon atoms. Illustrative of suitable alkoxyalkyl groups are methoxyethyl, methoxybutyl and methoxypropyl.

The aminoalkyl group represented by R and $R^1$ has 1 to 12 carbon atoms and is preferably represented by the following formula (6):

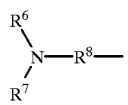

wherein $R^6$ and $R^7$ represent, independently from each other hydrogen or an alkyl group having 1 to 12 carbon atoms, preferably 1 to 4 carbon atoms, and $R^8$ represents an alkylene group having 1 to 6 carbon atoms, preferably 2 to 4 carbon atoms. Illustrative of suitable aminoalkyl groups are aminomethyl, aminoethyl, aminobutyl, N-methylaminoethyl, N,N-dimethylaminoethyl and N-methylaminobutyl.

The alkoxycarbonyl group represented by R and $R^1$ has 2 to 6 carbon atoms and is preferably represented by the following formula (7):

$$R^9OCO—$$

wherein $R^9$ represents an alkyl group having 1 to 6 carbon atoms, preferably 1 to 4 carbon atoms. Illustrative of suitable alkoxycarbonyl groups are methoxycarbonyl, ethoxycarbonyl and butoxycarbonyl.

The platinum complex of the formula (1) may be prepared by reacting a soluble platinum compound such as sodium tetrachloroplatinate with a ligand compound $L^1$ and then with a ligand compound $L^2$.

In the platinum complex of the formula (1), L represents a ligand selected from 2,2'-bipyridine compounds having at least one anionic group and 1,10-phenanthroline compounds having at least one anionic group. The anionic group may be the same as that described above with reference to the ligand $L^1$ or $L^2$ of the platinum complex of the formula (1).

$X^1$ and $X^2$ represent, independently from each other, a thiolate selected from those represented by the formulas (e) and (f) above, in which R represents an alkyl group having 1 to 6 carbon atoms, preferably 1 to 4 carbon atoms, an alkenyl group having 2 to 6 carbon atoms, preferably 2 to 4 carbon atoms, an alkoxyalkyl group having 2 to 12 carbon atoms, preferably 3 to 6 carbon atoms, an aminoalkyl group having 1 to 12 carbon atoms, preferably 1 to 8 carbon atoms, an alkoxycarbonyl group having 2 to 6 carbon atoms, preferably 2 to 4 carbon atoms, a cyano group or a hydrogen atom, and Ar represents a substituted or non-substituted aryl group having 6 to 10 carbon atoms, preferably 6 to 8 carbon atoms.

The alkyl group, alkoxyalkyl group, aminoalkyl group and alkoxycarbonyl group represented by R of the formula (e) may be the same as those described above with reference to the formulas (a) to (d). The alkenyl group represented by R may be, for example, vinyl or allyl.

The substituent for the aryl group represented by Ar may be a halogen atom, an amino group or a cyano group. Illustrative of suitable aryl groups are phenyl, tolyl, xylyl and naphthyl.

The platinum complex of the formula (2) may be prepared by reacting a soluble platinum compound such as sodium tetrachloroplatinate with a ligand compound L and then with ligand compound $X^1$ and $X^2$.

A dye-sensitized semiconductor electrode according to the present invention may be obtained by fixing the above-described platinum complex of the present invention to a film or layer of oxide semiconductor particles formed on an electrically conductive surface of a substrate in any suitable conventional manner.

As the substrate, there may be used a metal, such as titanium or tantalum, an electrically conductive glass or carbon.

As the oxide semiconductor, titanium oxide ($TiO_2$), zinc oxide (Zno), tin oxide ($SnO_2$), indium oxide ($In_2O_3$) and niobium oxide ($Nb_2O_5$). It is preferred that the oxide semiconductor have a large surface area for reasons of obtaining high performance of a solar cell. Thus, the oxide semiconductor preferably has a particle diameter of 1 to 200 nm, more preferably 50 nm or less. The oxide semiconductor preferably has a specific surface area of 5 to 100 $m^2/g$. The oxide semiconductor is immobilized on the conductive surface to form a generally porous film having a thickness of at least 200 nm, preferably 1,000 to 20,000 nm.

Fixation of the oxide semiconductor on the conductive surface may be effected by forming, by dipping, coating or any suitable known method, a layer of a suspension or slurry containing the oxide superconductor onto the conductive surface, followed by drying and calcination. A water medium which may contain a surfactant, a thickening agent such as polyethylene glycol and any suitable additive is generally used for forming the suspension or slurry. The calcinations is generally carried out at 300–900° C., preferably 400–800° C.

The platinum complex is fixed to the thus formed semiconductor layer. Thus, the platinum complex is dissolved in a suitable solvent such as methanol, ethanol, acetonitrile or dimethylformamide. The above-described semiconductor electrode is then impregnated with this solution by immersion, coating or any other suitably method. It is preferred that the solution penetrate deep into the porous layer of the oxide semiconductor. Thus, the semiconductor electrode is preferably evacuated at an elevated temperature to remove gases trapped therein. If the solution has a low concentration of the platinum complex, the impregnation procedure is repeated so that the semiconductor electrode is impregnated with a sufficient amount of the platinum complex. The platinum complex preferably forms a layer on surfaces of the oxide semiconductor.

A solar cell (dye-sensitized solar cell) according to the present invention is constructed from the above dye-sensitized semiconductor electrode, a counter electrode and an electrolyte solution (redox electrolyte) disposed between the above electrodes. Any suitable known electrolytes may be used for the purpose of the present invention. Illustrative of redox pairs are $I^-/I_3^-$, $Br^-/Br_3^-$ and quinone/hydroquinone pairs. In the case of $I^-/I_3^-$, for example, ammonium iodide and iodine may be used. As a solvent for the electrolyte, there may be used an electrochemically inert solvent capable of dissolving the electrolyte in a large amount, such as acetonitrile or propylene carbonate. Any suitable known counter electrode permitting reduction of oxidation-type redox may be used for the purpose of the present invention. A platinum electrode or a platinum-bearing electrode may be generally used.

The following examples will further illustrate the present invention.

EXAMPLE 1

Production of Platinum Complex

In 50 ml of water were dissolved 500 mg of sodium tetrachloroplatinate and 294 mg of 4,4'-dicarboxy-2,2'-bipyridine. The solution was boiled for 4 hours and then cooled to precipitate dichloro(4,4'-dicarboxy-2,2'-bipyridine. The precipitates were recovered by filtration and again dissolved in an aqueous potassium hydroxide alkaline solution. The alkaline solution was then acidified with a solution of quinoxaline-2,3-dithiolate, thereby obtaining a platinum complex having, as ligands, 4,4'-dicarboxy-2,2'-bipyridine (2,2'-bipyridine-4,4'-dicarboxylic acid) and quinoxaline-2,3-dithiolate.

Preparation of Sensitized Semiconductor Electrode

Commercially available $TiO_2$ semiconductor powder (P-25 manufactured by Japan Aerosol Inc., surface area: 55 $m^2/g$) was mixed with water containing acetyl acetone and a surfactant (triton X100) to obtain a slurry. The slurry was spread on an electrically conductive glass (F—$SnO_2$, 10 Ω/sq) and calcined at 500° C. for 1 hour in air to obtain an oxide semiconductor electrode. This was then immersed in an ethanol solution of the above platinum complex having a concentration of 100 mg/100 ml, and the solution was refluxed at 80° C. for 1 hour to absorb the platinum complex on the titanium oxide surface layer of the electrode. The electrode was then dried at room temperature to obtain a visible light-responsive electrode having a platinum complex-adsorbed titanium oxide porous film provided on a conductive glass surface.

Preparation of Solar Cell

A solar cell (size: 1 cm×1 cm) was fabricated using the above electrode and a counter electrode which was a platinum electrode obtained by vacuum-deposition of platinum on a conductive glass. The platinum layer had a thickness of 20 nm. An electrolyte solution to be placed between the two electrodes was a redox pair of $I^-/I^3$ obtained using tetrapropylammonium iodide (0.46M) and iodine (0.06M) as solutes and a mixed liquid of 80% by volume of ethylene carbonate and 20% by volume of acetonitrile.

Operation of Solar Cell

A potentiostat was used for measuring short-circuit electric current, open circuit voltage and fill factor.

It was found that the thus constructed solar cell gave a short-circuit electric current of 6.14 mA/cm², an open circuit voltage of 0.6 V and a fill factor FF of 0.71 under irradiation of AM1.5 using solar simulator light (100 mW/cm²). "AM1.5" corresponds to a solar beam with a zenith angle of 48 degrees. "FF" is a fill factor calculated from [maximum output/(short circuit electric current×open circuit voltage)].

EXAMPLE 2

Example 1 was repeated in the same manner as described above except that 4,7-dicarboxy-1,10-phenanthroline was substituted for 4,4'-dicarboxy-2,2'-bibpyridine. It was found that the solar cell gave a short-circuit electric current of 5.02 mA/cm², an open circuit voltage of 0.6 V and a fill factor of 0.76.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

The teachings of Japanese Patent Application No. 2000-064059, filed Mar. 8, 2000, inclusive of the specification, claims and drawings, are hereby incorporated by reference herein.

What is claimed is:

1. A platinum complex represented by the following formula (1):

$$PtL^1L^2 \tag{1}$$

wherein

L¹ represents a ligand selected from the group consisting of 2,2'-bipyridine compounds having at least one anionic group and 1,10-phenanthroline compounds having at least one anionic group and L² represents a dithiolate selected from the group consisting of those represented by the following formulas (a) through (d):

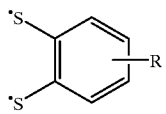

(a)

wherein R represents an alkyl group having 1 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano rup or a hydrogen atom,

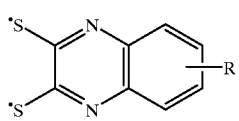

(b)

wherein R represents an alkyl group having 1 to 6 carbon atoms, an alkoxyalkyl group having 2 to 12 carbon atoms, an aminoalkyl group having 1 to 12 carbon atoms, an alkoxy carbonyl group having 2 to 6 carbon atoms, a cyano group or a hydrogen atom,

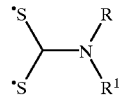

(c)

wherein R and R¹ represent, independently from each other, an alkyl group having 1 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom,

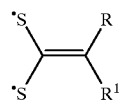

(d)

wherein R and R¹ represent, independently from each other, an alkyl group having 1 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom.

2. A platinum complex represented by the following formula (2):

$$PtLX^1X^2 \tag{2}$$

wherein

L represents a ligand selected from the group consisting of 2,2'-bipyridine compounds having at least one anionic group and 1,10-phenanthroline compounds having at least one anionic group and X¹ and X² represent, independently from each other, a thiolate selected from the group consisting of those represented by the following formulas (e) and (f):

$$.S-R \tag{e}$$

wherein R represents an alkyl group having 1 to 6 carbon atoms, an alkenyl group having 2 to 6 carbon atoms, an alkoxyalkyl group having 2 to 12 carbon atoms, an aminoalkyl group having 1 to 12 carbon atoms, an alkoxycarbonyl group having 2 to 6 carbon atoms, a cyano group or a hydrogen atom, $$.S-Ar \tag{f}$$

wherein Ar represents a substituted or non-substituted aryl group having 6 to 10 carbon atoms.

3. A dye-sensitized electrode comprising a substrate having an electrically conductive surface, an oxide semiconductor film formed on said conductive surface, and a platinum complex according to claim 1 supported on said film.

4. A dye-sensitized electrode comprising a substrate having an electrically conductive surface, an oxide semiconductor film formed on said conductive surface, and a platinum complex according to claim 2 supported on said film.

5. A solar cell comprising an electrode according to claim 3, a counter electrode, and an electrolyte disposed therebetween.

6. A solar cell comprising an electrode according to claim 4, a counter electrode, and an electrolyte disposed therebetween.

* * * * *

UNITED STATES PATENT AND TRADEMARK OFFICE
CERTIFICATE OF CORRECTION

PATENT NO. : 6,274,806 B1
DATED : August 14, 2001
INVENTOR(S) : Sugihara et al.

It is certified that error appears in the above-identified patent and that said Letters Patent is hereby corrected as shown below:

Column 5,
Line 37, "(Zno)" should read -- (ZnO) --.

Column 7,
Line 55, "rup" should read -- group --.

Signed and Sealed this

Twenty-third Day of April, 2002

Attest:

JAMES E. ROGAN
Attesting Officer  Director of the United States Patent and Trademark Office